(12) United States Patent
Weimann

(10) Patent No.: US 9,700,552 B2
(45) Date of Patent: Jul. 11, 2017

(54) PHARMACEUTICAL COMPOSITIONS FOR TREATMENT OF ADDICTION

(75) Inventor: Ludwig Jan Weimann, San Diego, CA (US)

(73) Assignee: Syntropharma Limited (GB)

( * ) Notice: Subject to any disclaimer, the term of this patent is extended or adjusted under 35 U.S.C. 154(b) by 985 days.

(21) Appl. No.: 12/920,058

(22) PCT Filed: Feb. 26, 2009

(86) PCT No.: PCT/GB2009/000537
§ 371 (c)(1),
(2), (4) Date: Nov. 30, 2010

(87) PCT Pub. No.: WO2009/106831
PCT Pub. Date: Sep. 3, 2009

(65) Prior Publication Data
US 2011/0064788 A1    Mar. 17, 2011

Related U.S. Application Data

(60) Provisional application No. 61/032,226, filed on Feb. 28, 2008.

(51) Int. Cl.
*A61F 13/00* (2006.01)
*A61K 9/70* (2006.01)
*A61K 31/485* (2006.01)
*A61K 47/14* (2017.01)

(52) U.S. Cl.
CPC .......... *A61K 31/485* (2013.01); *A61K 9/7084* (2013.01); *A61K 47/14* (2013.01)

(58) Field of Classification Search
CPC .... A61K 9/7023; A61K 9/703; A61K 9/7038; A61K 9/7046; A61K 9/7053; A61K 9/7069; A61K 9/7084; A61K 9/7092
USPC ................................. 424/448, 449
See application file for complete search history.

(56) References Cited

U.S. PATENT DOCUMENTS

| | | | |
|---|---|---|---|
| 4,626,539 A | 12/1986 | Aungst et al. | |
| 4,645,502 A | 2/1987 | Gale et al. | |
| 4,806,341 A * | 2/1989 | Chien et al. | 424/448 |
| 5,096,715 A | 3/1992 | Sinclair | |
| 5,149,538 A * | 9/1992 | Granger | A61K 9/703 |
| | | | 424/449 |
| 5,236,714 A | 8/1993 | Lee et al. | |
| 5,474,783 A | 12/1995 | Miranda et al. | |
| 5,985,317 A | 11/1999 | Venkateshwaran et al. | |
| 6,093,419 A | 7/2000 | Rolf | |
| 6,465,004 B1 * | 10/2002 | Rossi-Montero et al. | 424/448 |
| 6,569,449 B1 * | 5/2003 | Stinchcomb | A61K 9/7084 |
| | | | 424/443 |
| 7,182,955 B2 * | 2/2007 | Hart et al. | 424/449 |
| 2001/0006967 A1 | 7/2001 | Crain et al. | |
| 2001/0051166 A1 | 12/2001 | Luo et al. | |
| 2002/0004065 A1 | 1/2002 | Kanios | |
| 2002/0010127 A1 | 1/2002 | Oshlack et al. | |
| 2004/0013716 A1 * | 1/2004 | Gale | A61K 31/4535 |
| | | | 424/449 |
| 2004/0047901 A1 | 3/2004 | Beier et al. | |
| 2004/0126323 A1 | 7/2004 | Shevchuk et al. | |
| 2004/0219195 A1 | 11/2004 | Hart et al. | |
| 2006/0240085 A1 * | 10/2006 | Reidenberg et al. | 424/449 |
| 2008/0226698 A1 * | 9/2008 | Tang | A61K 9/7069 |
| | | | 424/448 |

FOREIGN PATENT DOCUMENTS

| | | |
|---|---|---|
| EP | 0 178 140 | 4/1986 |
| EP | 0 913 158 A1 | 5/1999 |
| WO | WO 88/09676 | 12/1988 |
| WO | WO 01/58447 | 8/2001 |
| WO | WO 03/059284 A2 | 7/2003 |
| WO | WO 03/070191 A1 | 8/2003 |
| WO | WO 03/103673 A1 | 12/2003 |
| WO | WO 2005/123046 | 12/2005 |
| WO | WO 2006/085521 A1 | 8/2006 |
| WO | WO 2007/016766 A1 | 2/2007 |
| WO | WO 2009/106831 A3 | 9/2009 |

OTHER PUBLICATIONS

International Search Report for International Application No. PCT/GB2009/000537 filed Feb. 26, 2009.
Tan, Hock S., et al. "Pressure-sensitive adhesives for transdermal drug delivery systems", PSTT vol. 2, No. 2, Feb. 1999, pp. 60-60.
Valiveti, Satyanarayana, et. al., In vivo evaluation of 3-O-alkyl ester transdermal prodrugs of naltrexone in hairless guinea pigs, www.sciencedirect.com; 2005, pp. 509-520.

* cited by examiner

*Primary Examiner* — Micah-Paul Young
(74) *Attorney, Agent, or Firm* — Berenato & White, LLC

(57) ABSTRACT

The invention provides transdermal patches comprising an adhesive and a composition comprising naltrexone and either methyl oleate or isopropyl myristate, a kit comprising a plurality of such transdermal patches, a composition comprising naltrexone and methyl oleate, such a composition for use as a medicament, and compositions comprising naltrexone and methyl oleate or isopropyl myristate for use in the treatment of alcoholism or opiate addiction.

20 Claims, 8 Drawing Sheets

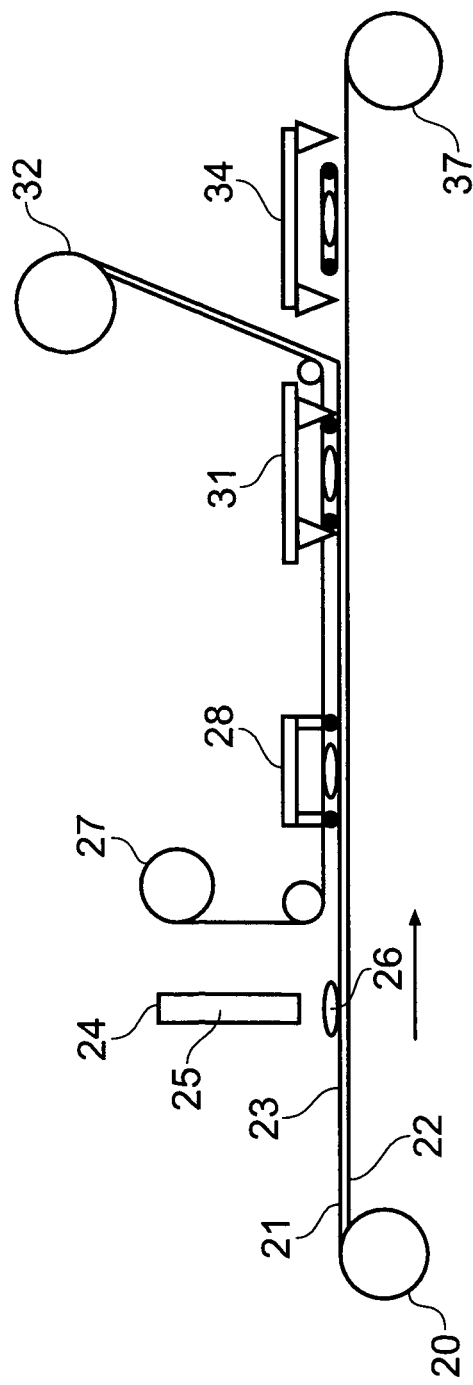
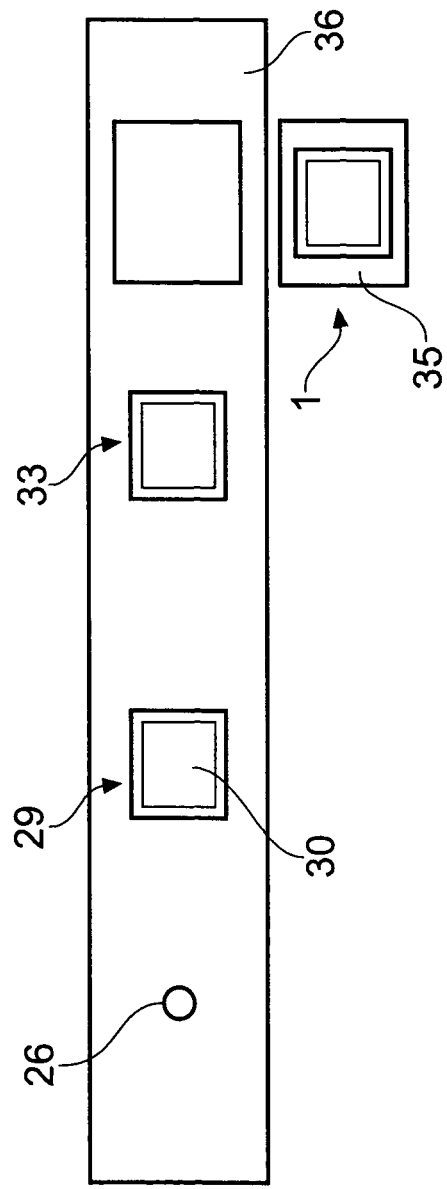
FIG. 4(a)
FIG. 4(b)

PHARMACEUTICAL COMPOSITIONS FOR TREATMENT OF ADDICTION

CROSS REFERECE TO RELATED APPLICATIONS

This application is a U.S. National phase under 35 U.S.C. §371 of International Patent Application No. PCT/GB2009/000537, filed Feb. 26, 2009, which claims the benefit of U.S. Application No. 61/032,226 filed Feb. 28, 2008, each of which is incorporated by reference in their entirety.

FIELD OF THE INVENTION

This invention relates to pharmaceutical compositions comprising the pharmaceutical naltrexone, an opioid receptor antagonist, and methods of using such compositions, in particular for the transdermal delivery of naltrexone. The compositions and methods of the invention have utility in a number of therapeutic interventions, in particular in the treatment of alcoholism and opiate addiction.

BACKGROUND OF THE INVENTION

Naltrexone is a well-known opioid receptor antagonist with no opioid agonist properties. Low doses of naltrexone have been investigated in patients with multiple sclerosis, autism, active Crohn's disease, AIDS, rheumatoid arthritis, celiac disease, certain forms of cancer, and autoimmune diseases. Opioids act as cytokines, the principal communication signallers of the immune system, creating immunomodulatory effects through opioid receptors on immune cells. Very low doses of naltrexone, of approximately one-tenth the usual dosage, boosts the immune system and helps to fight against diseases characterized by inadequate immune function. However naltrexone is used most commonly in the treatment of alcohol dependence (alcoholism) and opiate addiction.

In terms of pharmacology, naltrexone blocks the effects of opioids by its highly competitive binding at the μ-opioid receptors. Being a competitive antagonist, the suppression of an opiate's agonistic, euphorigenic effect can be overcome. However, clinical studies have indicated that naltrexone in an oral dosage of approximately 50 mg is able to block the pharmacological effects of up to 25 mg of intravenously administered heroin for periods as long as twenty four hours.

The mechanism of action of naltrexone in the treatment of alcoholism is not understood although involvement of the endogenous opioid system is suggested by pre-clinical data. Opioid antagonists have been shown to reduce alcohol consumption by animals, and naltrexone has shown efficacy in maintaining abstinence in clinical studies in humans.

Although well absorbed orally (approximately 96% of an oral dose is absorbed from the gastrointestinal tract), naltrexone is subject to significant first pass metabolism with oral bioavailability estimates ranging from 5% to 40%. The activity of naltrexone is believed to be as a result of both naltrexone and its 6-β-naltrexol metabolite. Two other minor metabolites are 2-hydroxy-3-methoxy-6-β-naltrexol and 2-hydroxy-3-methyl-naltrexone. Peak plasma levels of both naltrexone and 6-β-naltrexol occur within one hour after oral dosing; mean elimination half-life values for naltrexone and 6-β-naltrexol are four and thirteen hours respectively.

In terms of its use in the clinic, naltrexone tablets, as an adjunctive treatment of alcoholism, are typically used in a dosing regimen of 50 mg once daily for up to 12 weeks. A flexible approach to a dosing regimen tends to be employed to enhance patient compliance. Thus, patients may receive 50 mg of oral naltrexone every weekday, with a 100 mg dose on Saturday, or patients may receive 100 mg every other day, or 150 mg every third day. The systemic daily dose may vary between 2.5 and 20 mg, taking into account the oral dose and the bioavailability of naltrexone.

Whilst the oral administration of any drug has clear advantages, issues of patient non-compliance are particular concerns with the use of naltrexone in the treatment of alcoholism and for the treatment of opiate addiction. For example, naltrexone is a major liver toxin, which precludes oral administration in a significant number of alcoholics. Its long half-life also has the effect that there are significant quantities of it in the body after a period during the day when an alcoholic undergoing treatment may be permitted to drink. Clinicians generally prefer that a low build-up of an antagonist in the body before a session and its continued presence after the session should be avoided as much as possible. Accordingly, whilst naltrexone is the first new anti-alcoholism drug to receive approval from the Food and Drug Administration in the United States in many years, patient non-compliance, coupled with adverse gastro-intestinal effects, and variation in metabolic effects between even complying patients, limit the clinical usefulness of naltrexone.

As an alternative to oral administration, the use of depot injections of naltrexone have been investigated but such a way of administering of naltrexone is undesirable. For example, such depot injections are highly invasive and have additional pharmacological problems associated with inconsistent initial and sustained rates of delivery, inadequate release rates and site-of injection reactions. Nevertheless, injectable naltrexone is indicated or the treatment of alcohol dependence in patients who are able to abstain from alcohol in an outpatient setting prior to initiation of treatment. The recommended dose of 380 mg is administered intramuscularly every 4 weeks (once a month). This equates to an average daily dose is 12.5 mg with such a formulation.

In the treatment of opiate dependence, a dose of 50 mg once a day produces adequate clinical blockade of the actions of parenterally administered opiates. As with many non-agonist treatments for addiction, oral naltrexone is of proven value only when given as part of a comprehensive treatment plan that includes measures to ensure the patient compliance.

Naltrexone has very few and minor side effects, and may be the treatment of choice in highly motivated patients. However, clinical experience using oral naltrexone for treating opiate dependence has been replete with data of poor medication compliance according to several reports.

In conclusion, whilst naltrexone is available as once-a-day 50 mg oral tablets for the treatment of alcohol dependence and for opiate addiction, and as once-a-month injections for the treatment of alcohol dependence. There is a need to develop alternative non-invasive, controlled-released dosage formulations and methods of delivery for naltrexone as a consequence of the disadvantages reported above in relation to existing modes of naltrexone delivery using oral and injection-based deliveries.

Transdermal administration of drugs is often advantageous: it eliminates first-pass metabolism, and reduces gastro intestinal side-effects, and the invasiveness of the intramuscular depot injections known in the art. However, naltrexone does not present itself as an optimum or obvious candidate for transdermal delivery. This is, in part, as a consequence of the relatively high dosages required (for example between 2.5 mg and 20 mg per day) and because of a difficulty in achieving permeation through the skin, amongst other drugs. In EP-A-178140 (Alza Corporation) it is reported that the low permeability of naltrexone through the skin led to unsuccessful attempts to increase its permeation by the contemporaneous administration of conventional permeation enhancers. It is reported in that patent publication that the base form of naltrexone could be delivered through intact skin at fluxes capable of producing therapeutic effects if delivered in the presence of permeation-enhancing amounts of polyethylene-glycol monolaurate although this not in fact exemplified in the published application in respect of naltrexone.

Since the mid 1980s, when EP-A-178140 was published, there have been a large number of reports in relation to the search for a formulation capable of allowing effective transdermal delivery of naltrexone. Commonly, as an alternative to seeking delivery of the base form of naltrexone, efforts have focused on the development of lipophilic prodrugs of naltrexone for transdermal administration (for example naltrexone-3-(2' ethylbutyrate), naltrexone-3-valerate; naltrexone-ethyl butyryl ester and naltrexone dimethyl carbamate). Such prodrugs are hydrolyzed to naltrexone upon passing through the skin. For an example of a report regarding naltrexone prodrugs see S. Valiveti et al. (*J. Control. Release* 102, 509-520 (2005)).

SUMMARY OF THE INVENTION

We have surprisingly found, particularly in the light of the reports of attempts in the prior art to effect transdermal delivery of naltrexone, that certain pharmaceutical compositions comprising naltrexone and specific penetration enhancers, sometimes known and referred to as permeation enhancers, permit the transdermal delivery of therapeutically relevant quantities of naltrexone. In particular we have found that compositions comprising naltrexone in combination with the compounds methyl oleate and/or isopropyl myristate are useful in this regard, particularly when incorporated into patches suitable for adhesion to the skin of a patient.

Viewed from a first aspect, therefore, the invention provides a composition comprising naltrexone and methyl oleate.

Viewed from a second aspect the invention provides a transdermal patch comprising an adhesive and a composition comprising naltrexone and methyl oleate.

Viewed from a third aspect the invention provides a transdermal patch comprising an adhesive and a composition comprising naltrexone and isopropyl myristate.

Viewed from a fourth aspect the invention provides a composition according to the first aspect for use as a medicament.

Viewed from a fifth aspect the invention provides a composition according to the first or third aspects for use in the treatment of alcoholism.

Viewed from a sixth aspect the invention provides a composition according to the first or third aspects for use in the treatment of opiate addiction.

Viewed from a seventh aspect the invention provides a method of treatment of a human patient suffering from alcoholism comprising affixing a patch according to the second or third aspects of the invention to the skin of the patient whereby to effect transdermal delivery of naltrexone.

Viewed from an eighth aspect the invention provides a method of treatment of a human patient suffering from opiate addiction comprising affixing a patch according to the second or third aspects of the invention to the skin of the patient whereby to effect transdermal delivery of naltrexone.

Viewed from a ninth aspect the invention provides a kit comprising a plurality of patches according to the second or third aspects of the invention, wherein said patches are either the same or at least some differ from others in comprising a different quantity of naltrexone.

BRIEF DESCRIPTION OF THE DRAWINGS

FIG. 4(a) shows a schematic view of a manufacturing process of reservoir patches of the invention and FIG. 4(b) shows schematically the same process in plan.

DETAILED DESCRIPTION OF THE INVENTION

Figure 1A:
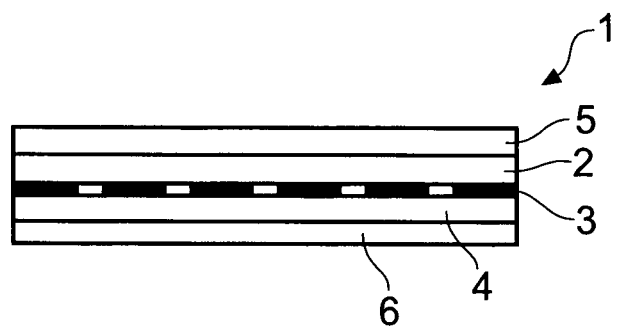
FIG. 1 shows a cross-sectional schematic representation of a fluid-reservoir (FIG. 1(a)), solid-reservoir (FIG. 1(b)) and monolithic (FIG. 1(c)) transdermal patches.

The present invention arises from the surprising finding that naltrexone-containing compositions comprising the compounds methyl oleate and/or isopropyl myristate are effective at permitting transdermal delivery into animals, in particular humans, typically from transdermal patches comprising such compositions that may be affixed to a subject's skin.

By transdermal herein is meant the passing through the skin and into a subject's blood stream, whereby to provide a systemic effect. Whilst the term embraces transmucosal, viz passing through mucosal tissue so as to embrace sublingual, buccal, vaginal and rectal delivery, typically transdermal delivery is effected through a subject's skin. For this reason, references are generally made herein to skin for simplicity's sake only although it will be appreciated that the transdermal delivery described herein may also be transmucosal.

By a patch or adhesive patch herein is meant material adapted for adhesion to a subject's skin or mucosal tissue. Typically patches herein have a substantial degree of rigidity and, in use, comprise a backing layer exposed to the environment and a naltrexone-containing composition beneath the backing layer. However, the patches of the invention may also be of a non-rigid nature, for example as described in U.S. Pat. No. 6,093,419.

According to the first aspect of the invention a composition is provided comprising naltrexone and methyl oleate. Such compositions may be presented in a number of different ways, a typical presentation being one that permits transdermal delivery. Examples of transdermal patches comprising naltrexone and methyl oleate are described hereinbelow. For example, the compositions may be contained within an adhesive patch designed to be affixed to the skin of a patient, or formulated into a capsule or sachet susceptible to easy rupture (e.g. by rubbing or squeezing between fingers) for release of a calculated dose of naltrexone formulation onto the skin into which it may be rubbed. Such sachets or capsules are disclosed in U.S. Pat. No. 5,096,715. Other formulations, such as topically applied gels, are known to the skilled person. Typically the compositions of the present invention comprising naltrexone and methyl oleate are presented as adhesive transdermal patches. Such patches comprising naltrexone and methyl oleate or isopropyl myristate constitute a delivery system for transdermal delivery of the naltrexone contained within them. Adhesive patches for the transdermal delivery of drugs are well known and have been described by H. S. Tan and W. R. Pfister in *Pressure-sensitive adhesives for transdermal drug delivery systems*, PSTT (Elsevier Science) Vol. 2. No. 2, February 1999.

Transdermal patches comprising the compositions of this invention contain a quantity of naltrexone and methyl oleate or isopropyl myristate to be delivered and an adhesive to allow contact between the patch and the skin to be maintained in absence of external pressure. Typically the patches comprise a first face that contacts the skin, and a protective backing layer on a second face of the patch opposing the first face, one face of the backing layer being exposed to the environment during use and comprising a material that is impervious to the components present in the patch. Attached to the first face of a transdermal patch is typically a releasable protective layer that protects the patch prior to its use and which may be released from the adhesive disposed at the first face of the patch prior to the patch being affixed to the skin.

Most transdermal patches according to this invention may be broadly divided into three categories: so-called fluid reservoir, solid reservoir and monolithic types. These are depicted in cross-section in FIG. 1.

FIG. 1(a) shows a fluid reservoir patch (1), the naltrexone-containing composition contained within being either dissolved or dispersed in a continuous matrix carrier (2), such as a fluid (typically a liquid) or a gel. The reservoir may be separated by a permeable membrane (3) from an adhesive layer (4). The rate-controlling membrane may be selected to control the rate at which the reservoir's contents are released to, and then through, the skin-contacting adhesive layer. The protective backing (5) and release (6) layers are also shown. The protective backing may be heat-sealed on the periphery that encloses/captures the liquid inside the reservoir.

Figure 1B:
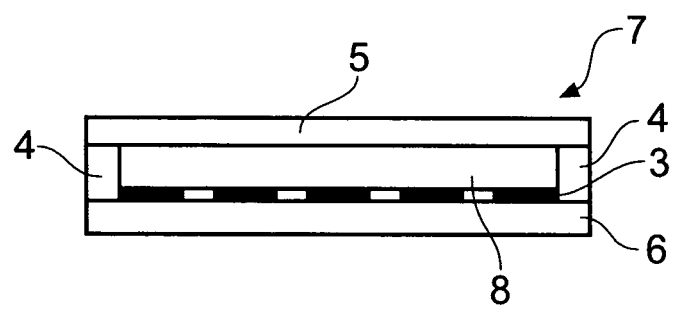

Solid reservoir patches (7), depicted in FIG. 1(b), are similar to the liquid-reservoir patches shown in FIG. 1(a) except that the adhesive (4) is not continuous across the area of the patch in contact with the skin when in use, but may be located at the periphery of the patch only. The solid reservoir may comprise a polymer matrix (8) from which the naltrexone-containing composition may be released. The nature of the polymer matrix in solid reservoir patches may serve to control the rate at which the naltrexone is delivered. Alternatively an optional rate-controlling membrane (3) may be present. FIG. 1(b) also shows the protective backing (5) and release (6) layers.

Figure 1C:
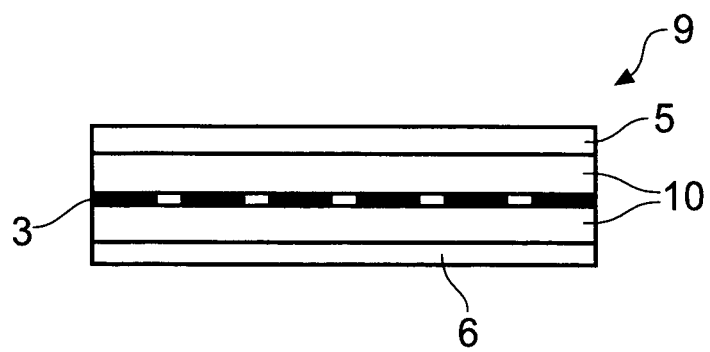

A monolithic patch (9) is shown in (FIG. 1(c)), showing the naltrexone composition and adhesive in intimate admixture (10). Whilst, analogously to the solid reservoir patches described above, the adhesive matrix through which the naltrexone containing composition is dissolved or dispersed may be used to control the rate at which the naltrexone is released, one or more optional rate-controlling membranes (3) may be present to provide a laminate, as opposed to a monolithic, structure. FIG. 1(c) shows a single such a membrane disposed between two layers (10) of adhesive/naltrexone-containing matrix. Alternatively there may be a plurality of such membranes (not shown) whereby to provide a multilaminate structure.

According to certain embodiments of the present invention, the naltrexone-containing compositions are presented in patches of the liquid reservoir, solid-reservoir and monolithic types. These embodiments are therefore now described in greater detail.

Most typically the monolithic patches are presented in a patch as depicted in cross-section in FIG. 1(c) but without the rate-controlling membrane (13). The monolithic patch construction typically comprises a protective backing layer (5), an adhesive matrix comprising the naltrexone-containing composition (10) and a releasable protecting layer (6) which may be removed, typically immediately prior to use of the patch. In use, therefore, the patch of the monolithic type typically comprises two parts: the adhesive- and naltrexone-containing layer; and the protective backing.

The releasable protecting layer, sometimes referred to in the art as a release liner, may be made of any convenient material. Appropriate materials are known in the art and include siliconised polyester or polyethylene materials, such as Scotchpak 9742, manufactured by 3M; and Bio-Release® and Syl-off® 7610 liners of Dow Corning Corporation. Other suitable release liners are available from both 3M and Dow Corning Corporation, and from other manufacturers.

The naltrexone- and adhesive-containing layer comprises naltrexone and methyl oleate or isopropyl myristate dispersed or dissolved in an adhesive matrix, more particularly a pressure-sensitive adhesive matrix. As is known in the art, a pressure-sensitive adhesive is a substance that forms a bond when pressure is applied between it and a surface, with the strength of the bond formed resultant from the amount of pressure used to apply the adhesive to the surface.

Suitable pressure-sensitive adhesives to use in transdermal delivery patches are well known to those skilled in the art and have been reviewed, for example, by Tan and Pfister (infra). Three types of adhesive are commonly employed in transdermal patches: polyisobutylenes, silicones and polyacrylate copolymers, although natural or synthetic rubber- or karya gum-based adhesives may also be used. Each of these four types of adhesive are commercially available, for example under the Roderm® (Rohm and Haas) DURO-TAK® (National Starch and Chemical Company) and BIO PSA® (Dow Corning) trade names.

Exemplary silicone pressure-sensitive adhesives are based on two major components: a polymer, or gum, and a tackifying resin. The silicone adhesive is usually prepared by cross-linking the gum, typically a high molecular weight polydiorganosiloxane, with the resin, to produce a three-dimensional silicate structure, via a condensation reaction in an appropriate organic solvent. The ratio of resin to polymer is the most important factor, which can be adjusted in order to modify the physical properties of polysiloxane adhesives. (see Sobieski et al., "Silicone Pressure Sensitive Adhesives", Handbook of Pressure-Sensitive Adhesive Technology, 2nd ed., pp. 508-517 (D. Satas, ed.), Van Nostrand Reinhold, New York (1989)). Suitable silicone pressure-sensitive adhesives are commercially available and include the silicone adhesives sold under the trademarks BIO-PSA® by Dow Corning Corporation, e.g. BIO-PSA® 7-4302.

In certain embodiments of the present invention the pressure-sensitive adhesive matrix comprises a polyacrylate copolymer. Such adhesives are used as such on account of their inherent tackiness. They are produced by copolymerisation of acrylic esters, acrylic acid and other functional monomers.

The term "polyacrylate copolymer" is used interchangeably here with the terms acrylic polymer, acrylate polymer, polyacrylate, polyacrylic adhesive and polyacrylate polymers as it is in the art.

Polyacrylates useful in practicing the invention are polymers of one or more monomers of acrylic acids and other copolymerizable monomers. The acrylic polymers also include copolymers of alkyl acrylates and/or methacrylates and/or copolymerizable secondary monomers or monomers with functional groups. By varying the amount of each type of monomer added, the cohesive properties of the resulting polyacrylate can be changed as is known in the art. In general, the polyacrylate is composed of at least 50% by weight of an acrylate or alkyl acrylate monomer, from 0 to 20% of a functional monomer copolymerizable with the acrylate, and from 0 to 40% of other monomers.

Acrylate monomers that can be used include acrylic acid, methacrylic acid, butyl acrylate, butyl methacrylate, hexyl acrylate, hexyl methacrylate, 2-ethylbutyl acrylate, 2-ethylbutyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the alkyl acrylates or methacrylates described above include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate and other monomers having at least one unsaturated double bond which participates in copolymerization reaction in one molecule and a functional group on its side chain such as a carboxyl group, a hydroxyl group, a sulfoxyl group, an amino group, an amino group and an alkoxyl, as well as a variety of other monmeric units including alkylene, hydroxy-substituted alkylene, carboxylic acid-substituted alkylene, vinylalkanoate, vinylpyrrolidone, vinylpyridine, vinylpyrazine, vinylpyrrole, vinylimidazole, vinylcaprolactam, vinyloxazole, vinylacetate, vinylpropionate and vinylmorpholine.

Further details and examples of acrylic adhesives which are suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, New York (1989) and are also described by Tan and Pfister (infra).

Examples of acrylic adhesives are acrylate or acrylate/vinyl acetate copolymers based on aliphatic monoacrylate monomers, e.g. butyl or 2-ethyl-hexyl acrylates and hydroxyl-aliphatic monoacrylate monomers e.g. hydroxyethyl acrylate, and vinyl acetate. An example of such an acrylic adhesive is DURO-TAK® 87-2510 sold by National Starch Company, Bridgewater, N.J.

Suitable acrylic adhesives are commercially available and include the polyacrylate adhesives sold under the trademarks DURO-TAK® by National Starch Company, Bridgewater, N.J., for example DURO-TAK® 87-608A, 900A AND 2510; GELVA® by Solutia, St. Louis, Mo.; HRJ by Schenectady International, Inc., Chicago, Ill.; and EUDRAGIT® by Roehm Pharma GmbH, Darmstadt, Federal Republic of Germany.

Typically, the pressure-sensitive adhesive matrix is a polyacrylate copolymer, since use of such matrices appear to permit higher transdermal fluxes of naltrexone (see the experimental results below). It is not completely understood why this is so; however, and without wishing to be bound by theory, such matrices have generally greater Hildebrand solubility parameters than other adhesives such as rubber-based or silicone adhesives.

As known by the skilled person, the Hildebrand solubility parameter, which is the square root of the cohesive energy of a substance, and provides an estimate of the degree of cohesion within a material. The Hildebrand solubility parameters quoted herein are calculated in accordance with the method described by Allan F. M. Barton in *Handbook of Solubility Parameters and Other Cohesion Parameters, 2nd* ed, CRC Press, 1991, at page 157.

We have surprisingly found that, generally, greater naltrexone fluxes achieved from the compositions of this invention when using adhesives of greater Hildebrand solubility parameter. Thus in certain embodiments of the invention adhesive matrices are employed that have Hildebrand solubility parameters in the range of 17 $(J/cm^3)^{1/2}$ or higher, for example Hildebrand solubility parameters in the range 17 to 25 $(J/cm^3)^{1/2}$, more particularly 19 to 25 $(J/cm^3)^{1/2}$, and more particularly still 19 to 21 $(J/cm^3)^{1/2}$. Adhesive matrices having such Hildebrand solubility parameters are typically, although not necessarily polyacrylate copolymers. Where matrices have similar Hildebrand solubility parameters, e.g. the polyacrylate copolymers DURO-TAK® 87-2510 and DURO-TAK® 900-A have Hildebrand solubility parameters of 19.7 and 19.5 $(J/cm^3)^{1/2}$ respectively as opposed to 14.9 $(J/cm^3)^{1/2}$ for the silicone adhesive BIO PSA® 7-4302, $(J/cm^3)^{1/2}$ the flux of naltrexone has a lower solubility. Thus in certain embodiments of the invention, typically wherein the adhesive matrix has a Hildebrand solubility parameter of greater than 17 $(J/cm^3)^{1/2}$ as described hereinbefore, the solubility of naltrexone in the matrix (typically a polyacrylate copolymer) may be in the range of about 2 to about 10 g of naltrexone/100 g of adhesive matrix, but in certain embodiments the adhesive matrix is chosen such that the solubility of naltrexone in it is less than about 5 g/100 g of adhesive, for example less than about 3 g/100 g of adhesive. Thus solubility ranges of 2 to 5, e.g. 2 to 3 g of naltrexone per 100 g of adhesive may be contemplated, particularly where the adhesive is [a polyacrylate copolymer], more particularly where such a polyacrylate copolymer has a Hildebrand solubility parameter the ranges of 17 to 25, more particularly still 19 to 25 $(J/cm^3)^{1/2}$ described hereinbefore. As an example, a monolithic matrix comprising DURO-TAK® 87-2510, in which 3.067 g of naltrexone is soluble in 100 g of polymer, has a much higher cumulative naltrexone flux than a corresponding patch in which DURO-TAK® 87-900A (Solubility of naltrexone =5.851 g/100 g of polymer) is used, even although the Hildebrand solubility parameters of these two adhesives are very similar. This data is presented in Example 5 and FIG. 7.

As an alternative to the adhesives described hereinbefore, it will be appreciated that, where it desired to affix a transdermal patch to a mucous membrane, it may be appropriate to use a mucoadhesive polymer. The mucoadhesive may be selected from one or more of sodium carboxymethyl cellulose, polyacrylic acid, such as sold under the designation Carbopol or polycarbophil, polyvinylpyrrolidone, polyethylene oxide, polyvinylmethylether/maleic anhydride copolymer, methyl cellulose, methylethyl cellulose, polyacrylamide, polyethyleneglycol, polyvinylalcohol, polyhydroxypropylcellulose and polyhydroxymethacrylate.

Where present, the rate-controlling membrane (3) may be any of those known to those skilled in the art. Suitable materials from which the rate-controlling membranes may be made include, but are not limited to, polyethylene; polypropylene; ethylene/propylene copolymers; ethylene/ethylacrylate copolymers; ethylene/vinyl acetate copolymers; polyacrylates; polymethacrylates; silicone elastomers; medical-grade polydimethylsiloxanes; neoprene rubber; polyisobutylene; chlorinated polyethylene; polyvinyl chloride; vinyl chloride-vinyl acetate copolymer; polymethacrylate polymer (hydrogel); polyvinylidene chloride; poly (ethylene terephthalate); butyl rubber; epichlorohydrin rubbers; ethylene-vinyl alcohol copolymer; ethylene-vinyloxyethanol copolymer; silicone copolymers, for example polysiloxane-polycarbonate copolymers, polysiloxane-polyethyleneoxidecopolymers, polysiloxane-polymethacrylate copolymers, polysiloxane-alkylene copolymers (e.g., polysiloxane-ethylene copolymers), polysiloxane-alkylenesilane copolymers (e.g., poly(siloxane-co-ethylenesilane), and the like; cellulose polymers, for example, methyl or ethyl cellulose, hydroxypropyl methyl cellulose, and cellulose esters; polycarbonates; polytetrafluoroethylene; starches; gelatin; natural and synthetic gums; any other natural or synthetic polymer or fiber; and combinations thereof. Examples include the 9% EVA rate-controlling membrane sold by 3M as CoTran 9702, or the microporous membrane sold by Solutech as Solupor 10P05A. Other rate-controlling membranes are known to those skilled in the art and/or are commercially available. Typically rate-controlling, or permeable, membranes have a porosity of 0.1 to 1 Å, e.g. about 0.5 Å.

The backing layer can be any suitable material that is impermeable to the contents of the reservoir compartment, the polymer matrix, or the adhesive matrix. Suitable materials for backing films are well known to those skilled in the art and include, but are not limited to, occlusive polymers such as polyurethane, polyesters such as poly(ethylene phthalate), polyether amide, copolyester, polyisobutylene, polyesters, high and low density polyethylene, polypropylene, polyvinylchloride, metal foils, and metal foil laminates of suitable polymer films. Such backing films are commercially available, e.g. under the Scotchpak® trade name from 3M, for example the 2 mil LDPE/PET laminate sold as Scotchpak® 9733.

The reservoir type patches from which naltrexone- and methyl oleate- or isopropyl myristate-containing formulations may be delivered are now described.

The releasable (6) and non-releasable (5) protecting layers of such patches may be of the same materials as described hereinbefore in respect of the corresponding layers of the monolithic type patches. The principal differences between the monolithic and liquid reservoir type patches is the presence in all embodiments of the latter (as opposed to only certain embodiments of the former) of a rate-controlling membrane and, of course, the presence of a solid or liquid reservoir comprising the naltrexone-containing composition. Whilst the adhesives used in such patches may be selected from the same adhesives described above in connection with the adhesives described in relation to the monolithic type patches, in particular the polyacrylate, silicone and adhesives described above, the adhesive is typically a silicone or rubber, e.g. polyisobutylene or styrene rubber adhesive, more usually a silicone or polyisobutylene rubber adhesive, most typically a silicone adhesive. The rate-controlling membrane may be any of those described above in connection with the monolithic type patches. Typically the matrix will be a fluid (normally liquid) matrix although it will be appreciated that polymeric matrices of the types described hereinabove may also be used.

Where the naltrexone-containing reservoir is a solid reservoir this may be made from a pharmacologically or biologically acceptable polymer matrix. Generally, the polymers used to form the polymer matrix are those capable of forming thin walls or coatings through which naltrexone can pass at a controlled rate. A non-limiting list of suitable materials for use as the polymer matrix includes polyethylene, polypropylene, ethylene/propylene copolymers, ethylene/ethylacrylate copolymers, ethylenevinyl acetate copolymers, silicones, rubber, rubber-like synthetic homo-, co- or block polymers, polyacrylic esters and the copolymers thereof, polyurethanes, polyisobutylene, chlorinated polyethylene, polyvinylchloride, vinyl chloride-vinyl acetate copolymer, polymethacrylate polymer (hydrogel), polyvinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluorethylene and mixtures thereof).

Where the naltrexone-containing reservoir is a liquid reservoir, this generally comprises a pure or aqueous alcohol, glycol or polyol, or mixture thereof. Typically the liquid reservoir comprises aqueous ethanol or aqueous isopropanol, most typically aqueous ethanol, in which the naltrexone and methyl oleate or isopropyl myristate may be dissolved. For example, aqueous solutions comprising from about 5% to 95% v/v ethanol and from about 95% to 5% v/v water may be used, e.g. about 40% to 60% v/v ethanol and from about 60% to 40% v/v water. Typically such aqueous solutions will comprise between about 80 and 95% v/v ethanol. The reservoirs (both liquid and solid) typically comprise naltrexone at saturated concentrations (generally achievable by using 5% to 15% naltrexone) with the dosage rate from the patch being determined not so much by the concentration of naltrexone in the solution but more or entirely by the porosity of the rate-controlling membrane. Alternatively subsaturated concentrations of naltrexone may be employed with the rate being controlled by the concentration of the naltrexone as well as the porosity of the rate controlling membrane.

Thus the quantity of naltrexone that may be used may be in a broad range from about 1% to about 15% or more, e.g. up to about 20% or even more, e.g. about 30% or 40%. These amounts are weight percentages with respect to the weight of the solid or liquid matrix within which the naltrexone is dissolved or dispersed. At concentrations in excess of 10% w/w, the naltrexone in the solid or liquid matrix tends to be past its saturation point and the matrices may contain crystallised, undissolved or precipitated naltrexone. This is an indication that the matrix is saturated and that the greatest transdermal flux is being achieved.

With monolithic patches, similar proportions of naltrexone may be used within the patches as described above with respect to the solid and liquid reservoirs, wherein the percentage naltrexone present is a weight percentage with respect to the weight of adhesive in the matrix. A monolithic matrix may be constructed by preparing a liquid adhesive solution or dispersion comprising, as an example, 40% solids and 60% solvent (e.g. aqueous ethanol), as well as dissolved or dispersed naltrexone. The monolithic patches may be made by drying such a preparation in an oven. Where the resultant matrix comprises 10 g of naltrexone and 90 g of adhesive—it will additionally contain methyl oleate or isopropyl myristate and, generally, a desired amount of solvent—such a concentration of naltrexone is referred to herein as 10 wt %.

As an alternative to the use of solution reservoirs, it will be understood to those skilled in the art that semisolid or hydrogel reservoirs may also be used in the patches described herein.

As is known by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally hydrogels comprise of crosslinked hydrophilic polymers such as polyurethanes, polyvinyl alcohols, polyacrylic acids, polyoxyethylenes, a polyvinylpyrrolidones, a poly(hydroxyethyl methacrylate) (poly(HEMA)), or a copolymer or mixture thereof. Alternatively a liquid reservoir may comprise a gelling agent, such as methyl cellulose, hydroxypropyl cellulose, hydroxylethyl cellulose, carboxyvinyl polymer. Such gels may be thixotropic, which can be advantageous during patch manufacture.

The amount of isopropyl myristate or methyl oleate affects the transdermal flux of naltrexone from all the formulations of naltrexone described herein. Accordingly, it will be understood that the amount of isopropyl myristate or methyl oleate can be varied to obtain a desired rate of transdermal flux of naltrexone. Typical amounts of isopropyl myristate or methyl oleate are from 1 to 20%, more usually 2 to 10%. These amounts are w/v with respect to the volume of solution used in the liquid reservoir embodiments and w/w with respect to the weight of the solid reservoir or adhesive matrix in the solid reservoir and adhesive matrix embodiments respectively.

In certain embodiments of the invention, where the naltrexone is presented in a composition comprising methyl oleate, this presentation is in intimate admixture with an adhesive. Thus the type of patch within the composition is contained, for use in transdermal delivery, is a patch of the monolithic type. In these and other monolithic patches of the present invention the adhesive present in the monolithic matrix comprising adhesive and naltrexone-containing composition is an acrylate adhesive.

With regard to those embodiments of the invention in which naltrexone is delivered from a composition comprising isopropyl myristate contained within a transdermal patch, this is preferably from a patch of the liquid reservoir type. In particular embodiments of the invention, including those in which liquid reservoir-containing patches comprise naltrexone and isopropyl myristate comprises a rate-controlling membrane having pore sizes within the range of about 0.1 to 1 Å. Typically, liquid reservoir-containing transdermal patches of the present invention employ a silicone adhesive although the other adhesives described herein may also be used.

The size of the patches may vary from about 1 $cm^2$ to greater than 200 $cm^2$; typically, patch sizes will cover an area of skin of approximately 5 to 50 $cm^2$. Methods of manufacturing transdermal patches are well known to those skilled in the art. For example, adhesive matrix systems can be prepared by casting a fluid admixture of adhesive, and solution or other mixture of naltrexone-containing composition onto the backing layer, followed by lamination of the release liner so as to provide a monolithic patch. Alternatively, the monolithic admixture may be cast on to the release liner, followed by lamination by the backing. Where the patch is of the reservoir type, the patch may be prepared in the absence of the naltrexone-containing composition, with the composition then added to the patch, for example by soaking aqueous ethanolic solution comprising naltrexone into a polymeric matrix adding such a solution to a void contained with the patch which may then be sealed. Exemplary manufacturing methods are described in the experimental section hereinafter.

In certain embodiments of the invention, an adhesive overlayer, which may also serve as the backing layer of the patches, may be used to secure the patch to the skin more robustly. Such overlayers may be of such a size that they extend beyond the drug-containing reservoir or matrix such that the adhesive on the overlayer comes into direct contact with an area of the skin surrounding the area of skin to which the naltrexone is delivered from the patch. The presence of such an overlayer can be useful where patches are to be worn by a patient for a prolonged period of time where the adhesive present in the patch might lose some of its adhesion due to hydration. Accordingly, by incorporation of such an adhesive layer, the patch can remain in place for a longer period of time. Alternatively, if the adhesive layer of the patch fails to provide adhesion for the desired period of time, it is possible to maintain contact between the dosage form with the skin by, for instance, affixing the dosage form to the skin of the patient with an adhesive tape, e.g., surgical tape.

In certain embodiments of the invention, it is appropriate to "operate", or use, the transdermal patch at an elevated temperature. With the liquid reservoir-containing transdermal patches in particular, it has been found that those containing naltrexone and isopropyl myristate effect twice as much delivery of naltrexone when the temperature of the patches increased from 32° C. to 42° C. The ability to provide an elevated temperature to transdermal patches is known to those skilled in the art. One example is a thin patch-like device placed over a medicament-containing transdermal patch, the overlaid secondary patch having a heat-generating system capable of maintaining the transdermal patch beneath at a constant elevated temperature. Appropriate overlying, heating patches are described in WO01/64150 (ZARS, Inc.) and are available from the company of the same name.

In order to administer the naltrexone contained within the patches described herein, the release liner is removed to expose the adhesive layer, be it a discrete layer or portion of adhesive as found, for example in the liquid or solid matrix patches described herein, or in admixture with a naltrexone-containing composition, as for example described in relation to the monolithic patches. Once the liner has been removed, the adhesive-containing layer is pressed against the skin of a subject to enable the naltrexone to penetrate through the skin of the subject. As noted above, with liquid reservoir-containing patches, the delivery rate of the naltrexone is generally controlled by the rate at which naltrexone passes through the rate-controlling membrane; with the monolithic and solid reservoir patches, the delivery rate generally as determined by the rate of diffusion of the naltrexone out of the solid (e.g. polymeric) matrix or naltrexone-containing adhesive composition.

The naltrexone-containing compositions of the present invention, in particular in the form of the transdermal patches described herein, may be administered to a patient in need thereof, in particular as part of a programme of medical intervention associated with the treatment of alcoholism or opiate addiction. It will be understood that alcoholism or opiate addiction are conditions ascertainable by medical practitioners and as used herein references to alcoholism or opiate addiction are to be understood as meaning a condition in which a subject is reliant upon alcohol or opiates to an extent that medical intervention is deemed to be appropriate by a medical practitioner.

It will be appreciated that the dosing regimen administrable by provision of the transdermally deliverable composition of the invention may be determined by an appropriate medical practitioner and that the dosage forms, and in particular the transdermal patches described herein, may contain varying amounts, or concentrations, of naltrexone. Patches or other transdermally deliverable compositions of this invention may be administered to any convenient area of skin on the patient. For example patches described herein may be applied to the arm, leg, back, front or other position upon a patient's body.

The present invention also provides an aspect in which the patches for practicing the methods or uses of the invention are conveniently provided in a kit form. In its simplest embodiment, a kit of the invention provides a plurality of patches at set dosages, wherein the dosages are set according to the needs of the patient. The patches may contain the same or different quantities or concentrations of naltrexone and may or may not be marked accordingly. Printed instructions on how to apply the patch, storage of the unit, and details of the treatment regimen may also be included in the kits. The kit may also be supplied with a overlying, heating patch as described hereinbefore, for use with the patches of the invention. Alternatively, one or more, e.g. all, of the patches of the kit may comprise such a heating patch.

A kit of the invention preferably includes packaging and printed instructions for its use, e.g., on the packaging or package insert. The naltrexone-containing patches within the kit may or may not be coded (i.e., colour, numerical by day, or numerical by dose, etc.) for the patient. For example, the printed instructions may describe the use of the dosage regiment to treat or prevent diarrhoea or other gastrointestinal conditions or disorders. The kit may include a disposal container i.e., any receptacle for holding material or device for disposal of used patches. Any such containers or devices known in the art can be used to prevent or limit potential abuse of the drug within the patch.

As known by those skilled in the art, the delivery profiles vary between different types of transdermal delivery patches. As exemplified within the examples that follow below, monolithic patches tend to show an initial lag time of approximately 8 to 10 hours before initial delivery. Thereafter, however, naltrexone flux is maintained at a steady state for several days. Accordingly, if it is desired to provide a patient with a patch suitable for delivery of naltrexone over a period of several days, for example, a monolithic-type patch may be appropriate. On the other hand, since liquid reservoir-containing patches tend to deliver the greatest quantity of naltrexone during an initial 24-hour period, if a medical practitioner wishes to supply patches for use on a daily basis, liquid-reservoir-containing patches, particularly those comprising isopropyl myristate, may be appropriate.

The invention is now further illustrated with reference to the following non-limiting examples:

1. Patch Design:

Two patch designs were tested for transdermal delivery in vitro:

Monolithic Patch

The monolithic transdermal patches described below comprise a pressure-sensitive adhesive matrix containing dissolved/dispersed naltrexone at a concentration close to saturation. On one (the adhesive) face of the matrix in each patch was provided a siliconised polyester release liner provided with a slit to aid in its removal prior to use. A typical manufacturing process for monolithic transdermal patches is as follows:

(I) Premixing of the Naltrexone in Solution

Naltrexone, optionally powdered, is added to an alcoholic solution, such as aqueous ethanol or aqueous isopropyl alcohol, typically whilst mixing. The naltrexone is present at such a concentration that a homogeneous mixture results. The methyl oleate or isopropyl myristate may be added during this first mixing step or during a subsequent mixing step in which the naltrexone-containing solution with a solution is contacted of adhesive whilst mixing, with mixing being continued until the mix is homogeneous.

(II) Coating and Lamination Procedures

Figure 3A:
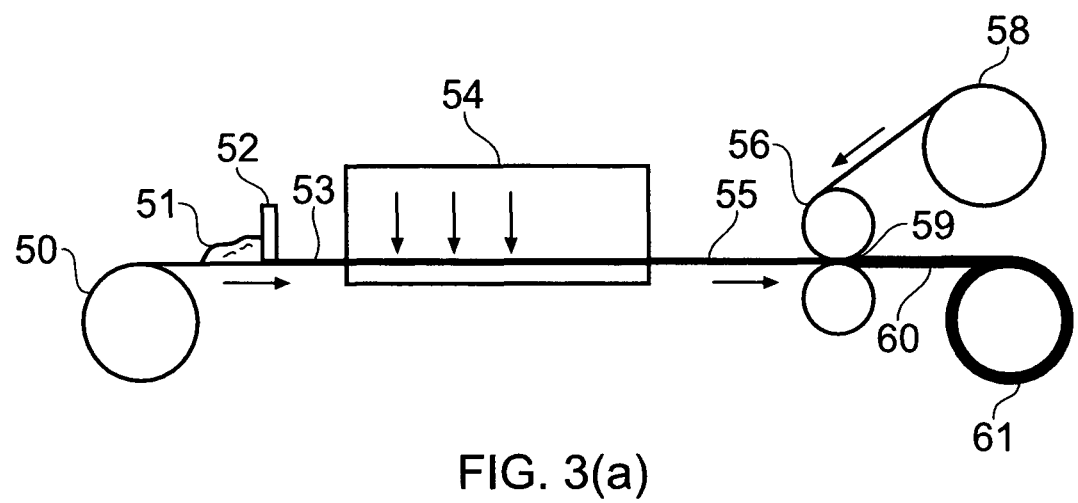
FIG. 3(a) shows schematically the coating and lamination steps involved in a process for manufacturing monolithic transdermal patches of the invention and FIG. 3(b) shows schematically the die-cutting of laminates resultant from FIG. 3(a) whereby to afford monolithic patches.

The coating and lamination procedures are illustrated in FIG. 3(a) in which wound siliconised 3 mil polyester liner (50) is unwound and a mixture of liquid adhesive with naltrexone and methyl oleate or isopropyl myristate (51) is added to the unwound release liner by a coating device the knife component of which is shown as (52). The action of the knife component (52) results in a thin layer (53) of the desired monolithic matrix. This then passes into a drying oven (54). The temperature is set in the drying oven at about 150° F. To begin the coating procedure, the oven is turned on. Oven air impingement rate and air exhaust is set according to established values. The adhesive blend containing dissolved or dispersed naltrexone is poured into the coating head (not shown). The coater's web is put in motion. The liquid layer of the adhesive blend is laid down (51) on the siliconized polyester by means of the coating knife (52) that allows consistent thickness of the liquid adhesive layer. The liquid adhesive layer on the polyester release liner when passing through the oven dries while the solvents evaporate completely forming a solid, tacky layer. This affords a liner coated with dried, tacky monolithic matrix (55) which passes to a lamination station (56) serving to unwind and laminate wound 3 mil polyolefin backing film (58) onto the coated liner while passing through laminating nip (59). The resultant laminate (60) is known as a "patch laminate". At this point of the coating process, a sample of the laminate is cut from the web and weighed to determine if product has the optimum coating weight determined by a specification for the intermediate patch laminate (60). Samples of the patch laminate (60) are also analyzed for drug content and residual solvents can be found (61).

Figure 3B:
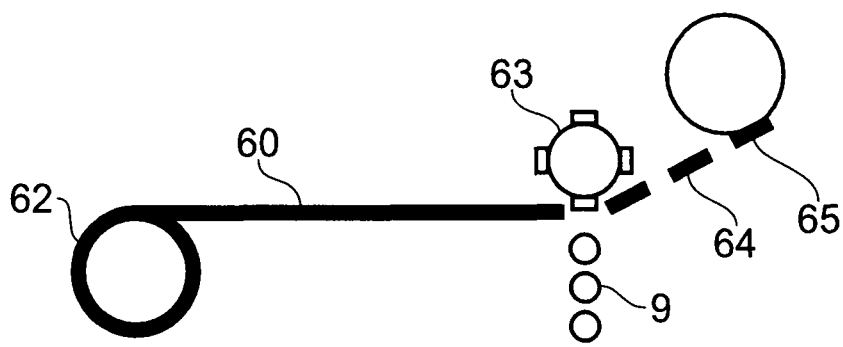

FIG. 3(b) shows unwinding of the patch laminate from the unwind shaft (62) of a die-cutting machine before the patch laminate (60) passes to the die or dies (63) where patch laminate (60) is cut to provide monolithic transdermal patches (9). These may be placed in pouches (not shown). Winding of the webbed waste laminate (64) is shown at winding station (65).

Reservoir Type Patch

Figure 2:
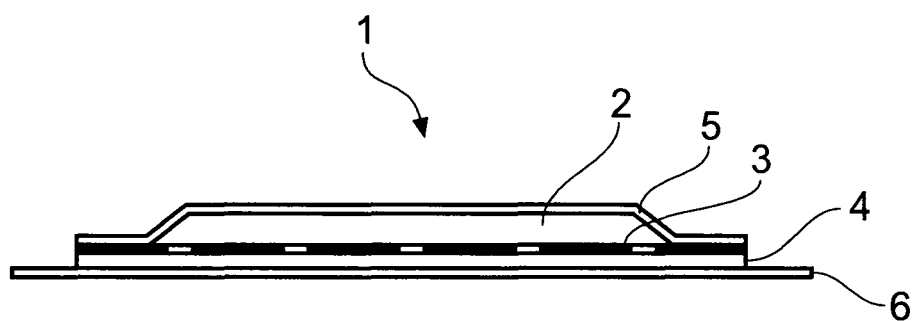
FIG. 2 is a cross-sectional schematic representation of a liquid-reservoir transdermal patch.

The liquid reservoir transdermal patches described below comprise components as illustrated in FIG. 2 wherein 6 is a release liner (Scotchpak 9742 (3M)); 4 is a skin contact adhesive (BIO PSA® 7-4302 (Dow Corning)); 3 is a drug permeable membrane (either 9% EVA, rate controlling membrane (CoTran 9702 from 3M) or microporous membrane (Solupor 10P05A from Solutech)); 5 is an occlusive backing laminate (2 mil LDPE/PET Scotchpak 9733 from 3M); and is a saturated solution of naltrexone in ethanol.

Typically, the materials used in the construction of reservoir-type transdermal patches are:
1. A controlled membrane laminate, which is a laminate of 3 mil PET release liner, 2 mil pressure-sensitive adhesive and 2 mil heat-sealable membrane film (typically 9% EVA or microporous LDPE);
2. A backing film, typically a heat-sealable polyester film composed of 1 mil LDPE and 2 mil PET; and
3. A gelled naltrexone-containing solution. Typically the naltrexone-containing solution is present in aqueous alcohol rendered thixotropic by the presence of a gelling agent. Typical gelling agents are hydroxyethyl cellulose, polyacrylic acid and sodium carboxymethyl cellulose. Others will be known to those skilled in the art.

A typical manufacturing process is shown schematically in FIG. 4. FIG. 4(a) shows the process schematically in elevation and FIG. 4(b) shows the process schematically in plan.

Thus FIGS. 4(a) and 4(b) show the unwinding of the controlled membrane laminate (20). The EVA membrane side (21) and PET side (22) of the unwound controlled membrane laminate (20) (23) are shown as the laminate advances towards pump station (24) delivering the typically thixotropic naltrexone-containing solution (25) in aliquots (26) onto the EVE membrane side (21) of the controlled membrane laminate (23). A reel (27) of backing film is unwound prior to heat-sealing within a heat-sealing station (28) having a given patch size tooling set. The heat-sealed package (29) with entrapped drug solution (30) then processes to a first die-cutting station (31) which kiss-cuts the package (29) on the EVA membrane side (21). The waste EVA membrane is collected (32) and the kiss-cut package (33) processes to a second die-cutting station (34) which effects cutting of the oversized release liner to afford the desired transdermal patch (1) optionally with an oversized release liner (35). Release liner waste (36) is collected (37).

2. In vitro Transdermal Flux Test Description:

In vitro transdermal flux testing was done using the Franz Diffusion Cell Method. (see B. W. Kemppainen and W. G. Reifenrath, "Methods for Skin Absorption", 1990, CRS Press, page 37).

Thinly microtomed human cadaver skin was obtained from a tissue bank. The skin was die-cut into small circles that fit the Franz cell diffusion area. Patches were placed on the top of the skin circles in contact with the stratum corneum, firmly pressed and then assembled with the Franz cell. Saline phosphate buffer of pH=7.4 was placed in the receiving chamber of the cell equipped with a small magnetic stirrer. Assembled Franz cells were placed on the top of magnetic stirrer located in the incubator set at 32° C. Aliquots of the receiving solution were withdrawn from the receiving chambers of the cells after 8, 24, 48, 72, 96 and 120 hrs and analyzed for content of naltrexone by HPLC method.

Figure 5:
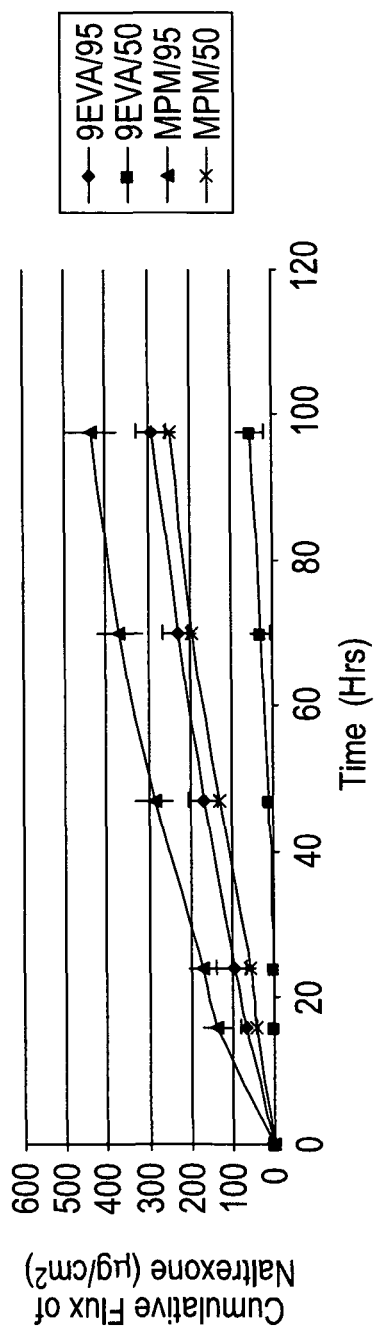
FIG. 5 shows the in vitro flux of naltrexone through human cadaver epidermis from different reservoir patches with saturated solutions in 95% ethanol and 50% ethanol (9EVA=9% EVA membrane, MPM=microporous membrane).

3. Initial Reservoir Patch Formulations and In Vitro Flux Results:

9EVA/95 Reservoir patch constructed with 9% EVA membrane and filled with saturated solution of naltrexone in 95% ethanol 9EVA/95 Reservoir patch constructed with 9% EVA membrane and filled with saturated solution of naltrexone in 50% ethanol MPM/95 Reservoir patch constructed with the microporous membrane Solupor 10P05A and filled with saturated solution of naltrexone in 95% ethanol MPM/50 Reservoir patch constructed with microporous membrane Solupor 10P05A and filled with saturated solution of naltrexone in 50% ethanol The reservoir patches described above were assembled and tested as described in Section 2. The fluxes achieved are plotted in FIG. 5 which shows that:

1. Transdermal flux of naltrexone was the highest from the reservoir patch constructed with the microporous membrane and filled with a saturated solution of naltrexone in 95% Ethanol. During the first 24 hrs it has been found to be 171 µg/cm$^2$; and
2. The predicted transdermal flux from a patch of 40 cm$^2$ would deliver 6.8 mg of naltrexone in 24 hrs.

Figure 6:
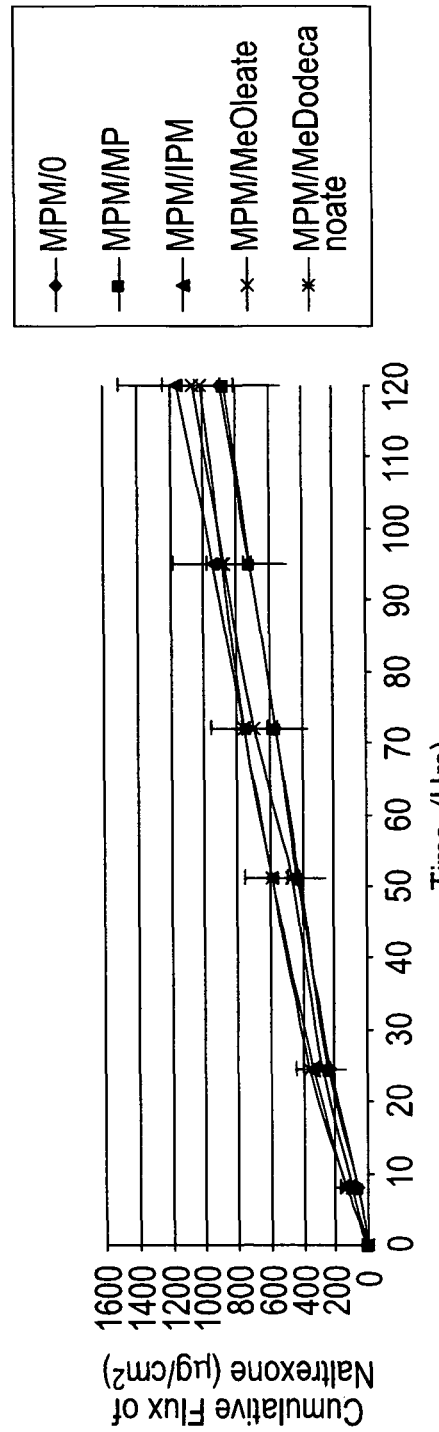
FIG. 6 shows the in vitro flux of naltrexone through human cadaver epidermis from reservoir patches with saturated solutions in 95% ethanol with and without added permeation enhancers (MPM=microporous membrane).

4. Reservoir Patch Formulations Containing Some Skin Permeation Enhancers and in vitro Flux Results:

In these patches a reservoir patch formulation constructed with microporous membrane and filled with a saturated solution of naltrexone in 95% ethanol was modified by the inclusion of the following permeation enhancers at 5% concentration:

| | | |
|---|---|---|
| a. | methyl pyrrolidone | (MP) |
| b. | isopropyl myristate | (IPM) |
| c. | methyl oleate | (MeOleate) |
| d. | methyl dodecanoate | (MeDodecanoate) | and the transdermal fluxes achieved plotted in FIG. 6 which shows that there is about 1.5 enhancement effect in naltrexone transdermal flux from the reservoir patch formulation containing 5% isopropyl myristate over formulation without any enhancer (MPM/0). Comparative transdermal flux rates are presented in the following table:

| Reservoir patch formulation | Naltrexone flux | |
|---|---|---|
| | First 24 hrs (mg/24 hrs/40 cm$^2$) | $2^{nd}$ to $5^{th}$ day (mg/24 hrs/40 cm$^2$) |
| Without enhancer | 9 | 6.5 |
| With 5% IPM | 13 | 8 |

The naltrexone transdermal flux results from reservoir patch formulations show a "burst" effect evidenced by the highest flux occurring during the initial 24 hours with about a 30% flux decrease but, nevertheless, at steady state over the next 4 days.

5. Initial Monolithic Patch Formulations and in vitro Flux Results:

Typical Monolithic Patch Formula:

| | Per solids | Per liquid |
|---|---|---|
| Adhesive | 90 parts | 90 parts/% solids |
| Naltrexone | 10 parts | 10 parts |
| Ethanol | 20 parts | 20 parts |

Adhesives used (Hildebrand solubility parameter, in $(J/cm^3)^{1/2}$ in parentheses):
 a. DURO-TAK® 87-608A (16.6) (PIB Rubber) National Starch
 b. DURO-TAK® 900A (19.5) (Acrylic) National Starch
 c. DURO-TAK® 87-2510 (19.7) (Acrylic) National Starch
 d. BIO PSA® 7-4302 (14.9) (Silicone) Dow Corning
 e. Roderm® MD-153 (17.6) (Styrene) Rohm and Haas.

Figure 7:
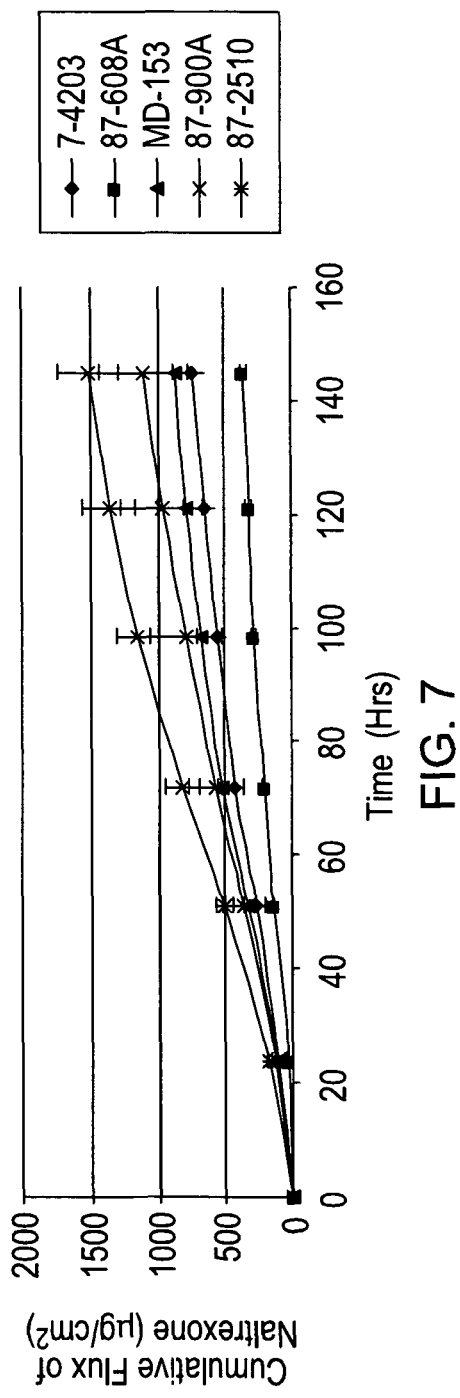
FIG. 7 shows the in vitro flux of naltrexone through human cadaver epidermis from different monolithic patches, each containing 10% naltrexone.

The transdermal fluxes achieved are plotted in FIG. 7 which shows that two formulations show the best transdermal flux of naltrexone over 5 days after the first day, namely DURO-TAK® 87-900A (9.2 mg/24 hrs/40 cm$^2$) and DURO-TAK® 87-2510 (12.4 mg/24 hrs/40 cm$^2$). All monolithic patches tested show a lag time of about 10 hours. However, after the first 24 hours the naltrexone flux holds at steady state for the next 4 days.

6. Comparison of Naltrexone in vitro Transdermal Flux from Reservoir Patch Formulation with IPM Enhancer and from Monolithic Patch Based on DURO-TAK® 87-2510 Adhesive.

Figure 8:
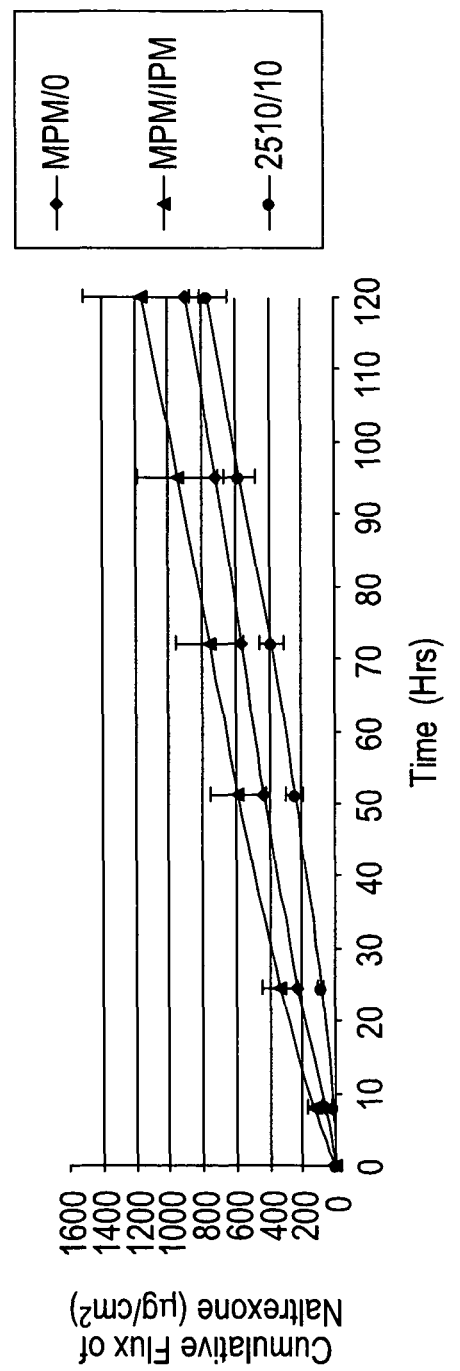
FIG. 8 shows a comparison of the in vitro flux of naltrexone through human cadaver epidermis from reservoir patches and a monolithic patch based on DURO-TAK® 87-2510 adhesive with 10% naltrexone (shown as 2510/10).

The in vitro flux experiment was run using the same cadaver skin for both the reservoir patch formulation with IPM as an enhancer side-by-side with the monolithic patch based on DURO-TAK® 87-2510 adhesive. The cumulative flux results are presented graphically in FIG. 8. The in vitro flux of naltrexone per 24 hours from different 40 cm$^2$ patches was calculated from the slope of kinetic graphs and the results are as follows:

| Reservoir Patch without enhancer | 7.1 mg |
|---|---|
| Reservoir Patch with 5% IPM enhancer | 9.1 mg |
| Monolithic Patch of DURO-TAK ® 87-2510 adhesive with 10% naltrexone (without enhancer) | 6.1 mg |

Thus the in vitro flux of naltrexone from reservoir patch filled with ethanol saturated solution of naltrexone with 5% IPM enhancer is about 50% higher than the naltrexone flux from a monolithic patch based on DURO-TAK® 87-2510 adhesive.

7. In vitro Transdermal Flux of Naltrexone from Monolithic Patches Based on DURO-TAK® 87-2510 Adhesive Containing Different Enhancers at 5% Concentration.

| | 0 | 10 | 29 | 48.5 | 73 | 96.5 | 120 |
|---|---|---|---|---|---|---|---|
| 2510/10/0 | 0 | 44 | 188 | 348 | 481 | 818 | 1048 |
| 2510/10/IPM | 0 | 26 | 192 | 339 | 477 | 714 | 907 |
| 2510/10/MO | 0 | 87 | 280 | 481 | 710 | 1045 | 1359 |
| 2510/10/MDD | 0 | 63 | 225 | 374 | 511 | 768 | 1025 |
| 2510/10/MP | 0 | 52 | 205 | 350 | 486 | 748 | 1007 |
| MPM/95/IPM | 0 | 266 | 474 | 633 | 812 | 1314 | 1792 |
| std | 0 | 46 | 105 | 181 | 159 | 261 | 329 |
| std | 0 | 14 | 60 | 112 | 169 | 184 | 205 |
| std | 0 | 3 | 64 | 166 | 315 | 471 | 598 |
| std | 0 | 54 | 72 | 85 | 99 | 122 | 178 |
| std | 0 | 45 | 60 | 51 | 40 | 29 | 55 |
| std | 0 | 60 | 92 | 75 | 92 | 28 | 96 |

Figure 9:
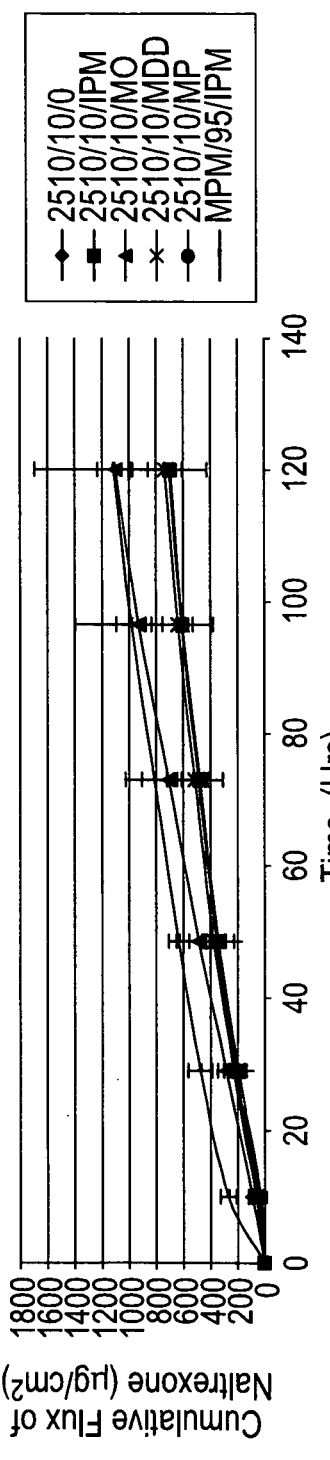
FIG. 9 shows the in vitro flux of naltrexone through human cadaver epidermis from monolithic patches based on DURO-TAK® 87-2510 adhesive containing 10% naltrexone with different skin penetration enhancers at 5% (shown as 2510/10/X where X denotes the abbreviated name for the enhancer) compared with one reservoir patch (MPM/95/IPM) containing naltrexone-saturated ethanol solution containing 5% isopropyl myristate.

The data is plotted in FIG. 9 in which MPM/95/IPM is a reservoir patch with microporous membrane filled with naltrexone saturated ethanol solution containing 5% isopropyl myristate; and 0=no enhancer
IPM=isopropyl myristate
MO=methyl oleate
MDD=methyl dodecanoate
MP=methylpyrrolidone

CONCLUSIONS

Addition of enhancers to the DURO-TAK® 87-2510 did not improve the transdermal flux except from the formulation with methyl oleate. The in vitro flux of naltrexone per 24 hours from different 40 cm$^2$ patches calculated from the slope of kinetic graph is 9.4 mg All monolithic patches are still showing an 8-10 hours lag time.

During the first 24 hours after application of the patch to skin, the naltrexone flux from the reservoir patch formulation containing saturated naltrexone solution in ethanol and 5% IPM is the highest.

Therefore, if one wants to have a one-day patch, one should go with the reservoir patch formulation.

However, if one wants a 7-day patch and the lack of patch efficacy during the first 24 hrs is not of a great concern, the transdermal flux of naltrexone from the monolithic patch with Methyl Oleate is as good as from reservoir patch.

8. Temperature Effect on Transdermal Flux of Naltrexone from Monolithic Patches and Reservoir Patches with Microporous Membrane

| | 32° C. 0 | 32° C. 10 | 32° C. 29 | 32° C. 48.5 | 32° C. 73 | 42° C. 96.5 | 42° C. 120 |
|---|---|---|---|---|---|---|---|
| 2510/10/0 | 0 | 44 | 188 | 348 | 481 | 818 | 1048 |
| 2510/10/IPM | 0 | 26 | 192 | 339 | 477 | 714 | 907 |
| 2510/10/MO | 0 | 87 | 280 | 481 | 710 | 1045 | 1359 |

-continued

|  | 32° C. 0 | 32° C. 10 | 32° C. 29 | 32° C. 48.5 | 32° C. 73 | 42° C. 96.5 | 42° C. 120 |
|---|---|---|---|---|---|---|---|
| 2510/10/MDD | 0 | 63 | 225 | 374 | 511 | 768 | 1025 |
| 2510/10/MP | 0 | 52 | 205 | 350 | 486 | 748 | 1007 |
| MPM/95/IPM | 0 | 266 | 474 | 633 | 812 | 1314 | 1792 |
| std | 0 | 46 | 105 | 181 | 159 | 261 | 329 |
| std | 0 | 14 | 60 | 112 | 169 | 184 | 205 |
| std | 0 | 3 | 64 | 166 | 315 | 471 | 598 |
| std | 0 | 54 | 72 | 85 | 99 | 122 | 178 |
| std | 0 | 45 | 60 | 51 | 40 | 29 | 55 |
| std | 0 | 60 | 92 | 75 | 92 | 28 | 96 |

Figure 10:
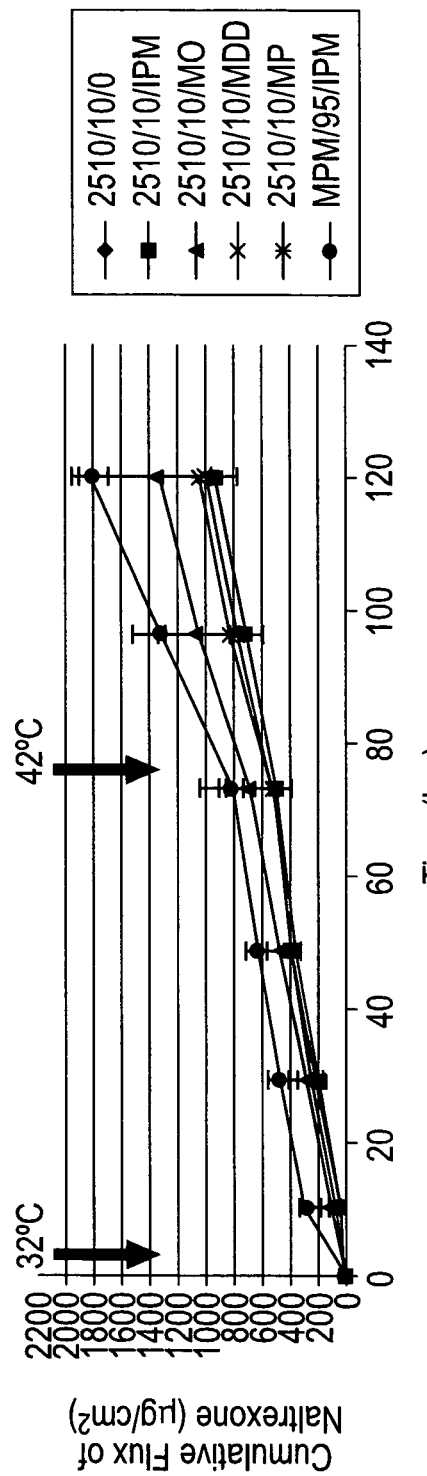
FIG. 10 shows the effect of patch and skin temperature on in vitro flux of naltrexone through human cadaver epidermis from monolithic patches based on DURO-TAK® 87-2510 adhesive containing 10% naltrexone with different skin penetration enhancers at 5% (shown as 2510/10/X where X denotes the abbreviated name for the enhancer) compared with one reservoir patch (MPM/95/IPM) containing naltrexone-saturated ethanol solution containing 5% isopropyl myristate.

The above data is plotted in FIG. 10

Figure 11:
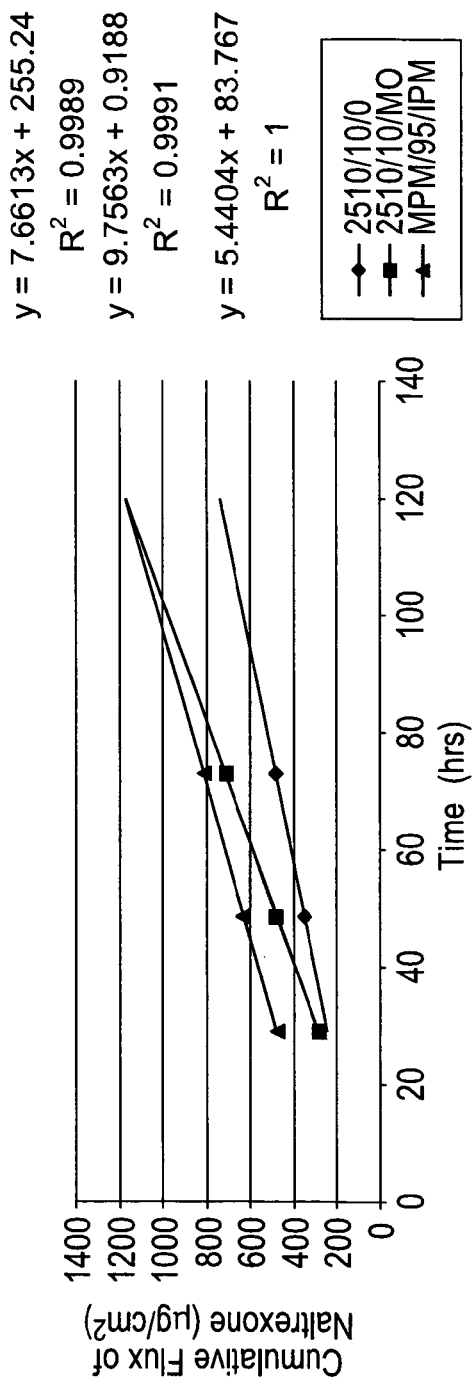
FIG. 11 shows in vitro flux of naltrexone through human cadaver epidermis from monolithic patches of DURO-TAK® 87-2510 containing 10% naltrexone with and without methyl oleate enhancer and from reservoir patch MPM/95/IPM at 32° C.

FIG. 11 shows in vitro flux of naltrexone through human cadaver epidermis from monolithic patches of DURO-TAK® 87-2510 containing 10% naltrexone (saturated level) with and without methyl oleate enhancer and from reservoir patch MPM/95/IPM at 32° C.

Figure 12:
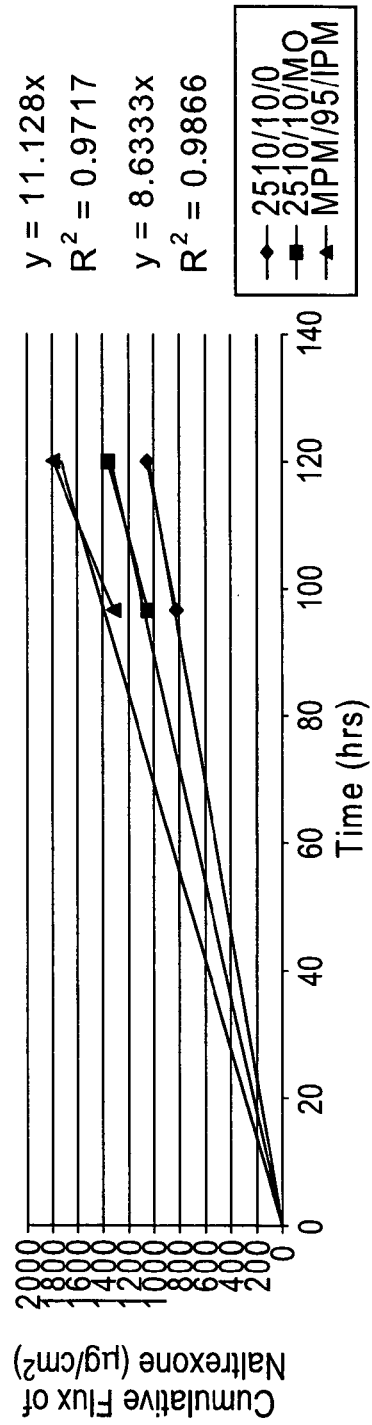
FIG. 12 shows in vitro flux of naltrexone through human cadaver epidermis from monolithic patches of DURO-TAK® 87-2510 containing 10% naltrexone with and without methyl oleate enhancer and from reservoir patch MPM/95/IPM at 42° C.

FIG. 12 shows in vitro flux of naltrexone through human cadaver epidermis from monolithic patches of DURO-TAK® 87-2510 containing 10% naltrexone (saturated level) with and without methyl oleate enhancer and from reservoir patch MPM/95/IPM at 42° C.

SUMMARY

| Naltrexone Flux (µg/cm2/hr) | | |
|---|---|---|
|  | 32° C. | 42° C. |
| 2510/10/0 | 5.4 | 8.6 |
| 2510/10/MO | 9.8 | 11.1 |
| MPM/95/IPM | 7.7 | 14.4 |

| Naltrexone Flux (mg/40 cm$^2$/24 hrs) | | |
|---|---|---|
|  | 32° C. | 42° C. |
| 2510/10/0 | 5.2 | 8.3 |
| 2510/10/MO | 9.4 | 10.7 |
| MPM/95/IP | 7.4 | 13.8 |

CONCLUSIONS

1. Increase of temperature of the transdermal patch and skin by 10° C. (from 32° C. to 42° C.) increases in vitro transdermal flux of naltrexone from monolithic patch without enhancers. naltrexone flux almost doubles from monolithic patch of DURO-TAK® 87-2510 adhesive matrix containing 10% naltrexone (saturated) without an enhancer.

2. Naltrexone flux from monolithic patch of DURO-TAK® 87-2510 adhesive matrix with 5% methyl oleate as an enhancer is not affected by increase of the temperature.

3. Naltrexone flux from reservoir patch filled with ethanol-saturated solution of naltrexone and 5% IPM doubles when the temperature is increased from 32° C. to 42° C.

The invention claimed is:

1. A transdermal patch comprising an adhesive and a composition comprising naltrexone and methyl oleate, wherein the naltrexone and the methyl oleate of the composition are contained in a common matrix of the transdermal patch.

2. The transdermal patch as claimed in claim 1 wherein the composition comprises about 1 to about 20% of methyl oleate.

3. The transdermal patch as claimed in claim 1 wherein the composition comprises from about 1 to about 15% of naltrexone.

4. The transdermal patch as claimed in claim 1 wherein the matrix comprises the composition dissolved or dispersed in a carrier and the transdermal patch comprises the adhesive in a separate layer to the matrix containing the composition.

5. The transdermal patch as claimed in claim 1 wherein the composition is in intimate admixture with the adhesive in the matrix.

6. The transdermal patch as claimed in claim 4 wherein the carrier is selected from the group consisting of a polymer matrix, a liquid, aqueous alcohol, and aqueous ethanol.

7. The transdermal patch as claimed in claim 1 that further comprises a naltrexone-permeable membrane layer.

8. The transdermal patch according to claim 4 further comprising permeable membrane layer present between the carrier comprising the composition and the layer of adhesive.

9. The transdermal patch as claimed in claim 7 wherein the naltrexone-permeable membrane layer has a porosity between about 0.1 and 1Å.

10. The transdermal patch as claimed in claim 1 wherein the adhesive is selected from the group of a rubber, a silicone, and a polyacrylate copolymer.

11. The transdermal patch as claimed in claim 10 wherein the adhesive has a Hildebrand solubility parameter of more than about 17 $(J/cm^3)^{1/2}$.

12. The transdermal patch as claimed in claim 10 wherein the solubility of naltrexone in the adhesive is between about 2 and about 10 g of naltrexone per 100 g of adhesive.

13. The transdermal patch as claimed in claim 1 further comprising a heat-generating system for elevating the temperature of the composition.

14. A method of treatment of a human patient suffering from alcoholism or opiate addiction, comprising affixing the transdermal patch as defined in claim 1 to the skin of the patient thereby effecting transdermal delivery of naltrexone.

15. A kit comprising at least two transdermal patches as claimed in claim 1.

16. The kit as claimed in claim 15 wherein at least one transdermal patch further comprises a heat-generating system for elevating the temperature of the compositions in the transdermal patch.

17. The transdermal patch as claimed in claim 1 wherein the naltrexone and the methyl oleate of the composition are mixed with one another.

18. The transdermal patch as claimed in claim 1 wherein the matrix is in a liquid or gel state and contained in a reservoir.

19. The transdermal patch as claimed in claim 1 wherein the transdermal patch is a monolithic patch comprising a protective backing layer, a releasable protecting layer, and the matrix interposed between the protective backing layer and the releasable protecting layer, and wherein the adhesive, the naltrexone, and the methyl oleate are intimately admixed with one another in the matrix.

20. The transdermal patch as claimed in claim 1 wherein the matrix comprises the composition dissolved in a carrier.

* * * * *